(12) United States Patent
Harris et al.

(10) Patent No.: US 8,783,870 B2
(45) Date of Patent: Jul. 22, 2014

(54) HANDHELD TELEPHONY DEVICE FOR FIELD SOBRIETY TESTING

(71) Applicant: Enforcement Innovations, Austin, TX (US)

(72) Inventors: Royger Paul Harris, Austin, TX (US); Doyle Eugene Hobbs, Hutto, TX (US)

(73) Assignee: Enforcement Innovations, Austin, TX (US)

( * ) Notice: Subject to any disclaimer, the term of this patent is extended or adjusted under 35 U.S.C. 154(b) by 0 days.

(21) Appl. No.: 14/013,337

(22) Filed: Aug. 29, 2013

(65) Prior Publication Data

US 2014/0002798 A1    Jan. 2, 2014

Related U.S. Application Data

(60) Division of application No. 13/667,587, filed on Nov. 2, 2012, which is a continuation of application No. 12/837,960, filed on Jul. 16, 2010, now Pat. No. 8,317,328.

(60) Provisional application No. 61/230,009, filed on Jul. 30, 2009.

(51) Int. Cl.
*A61B 3/14*  (2006.01)
*A61B 3/10*  (2006.01)

(52) U.S. Cl.
USPC ............................. 351/210; 351/218; 351/221

(58) Field of Classification Search
USPC .................................................. 351/200–246
See application file for complete search history.

(56) References Cited

U.S. PATENT DOCUMENTS

| | | | |
|---|---|---|---|
| 7,309,125 B2 | 12/2007 | Pugach et al. | |
| 7,338,166 B2 | 3/2008 | Waldorf et al. | |
| 7,519,864 B2 * | 4/2009 | Alam et al. | 714/32 |
| 7,819,527 B2 | 10/2010 | Bardenstein et al. | |
| 8,064,886 B2 * | 11/2011 | Hawkins et al. | 455/413 |
| 8,226,574 B2 | 7/2012 | Whillock et al. | |
| 8,317,328 B1 * | 11/2012 | Harris et al. | 351/210 |
| 2010/0280372 A1 | 11/2010 | Poolman et al. | |

* cited by examiner

*Primary Examiner* — Mohammed Hasan
(74) *Attorney, Agent, or Firm* — Meyertons Hood Kivlin Kowert & Goetzel, P.C.; Jeffrey C. Hood; Stephen A. Mason

(57) ABSTRACT

Various embodiments of a device for performing a gaze field sobriety test are disclosed. The device includes a housing. A light source is affixed in or on the housing. The light source generates light during at least a portion of the gaze field sobriety test. A speaker positioned in or on the housing generates sounds during at least a portion of the gaze field sobriety test. A power source is coupled to the speaker and the light source. An input is positioned on the housing. The input is selectable by a test administrator to initiate an audible sound through the speaker at a predetermined time interval during at least a portion of the gaze field sobriety test. The audible sound provides an indication to the test administrator during the gaze field sobriety test to assist in proper performance of the gaze field sobriety test.

20 Claims, 9 Drawing Sheets

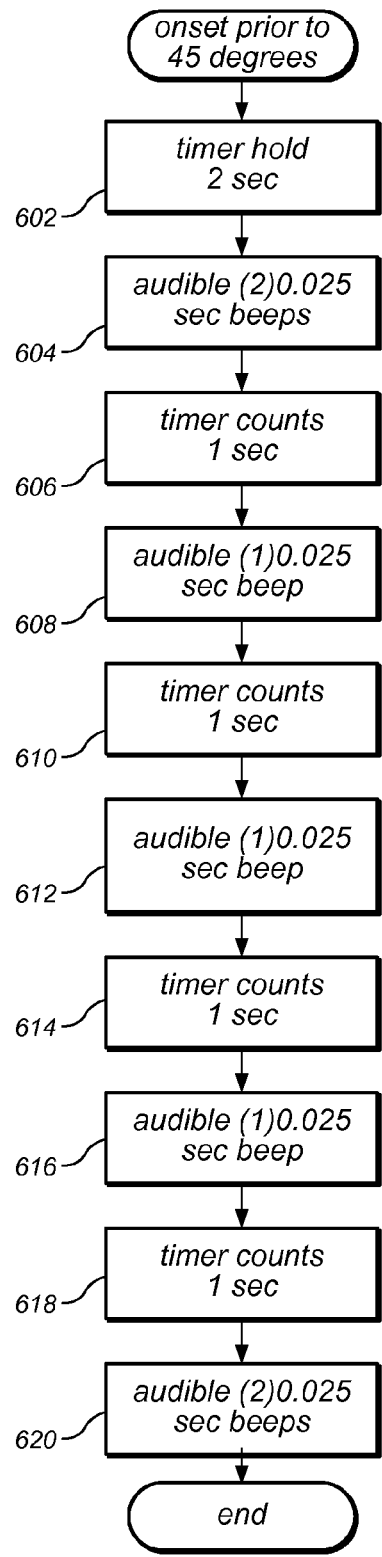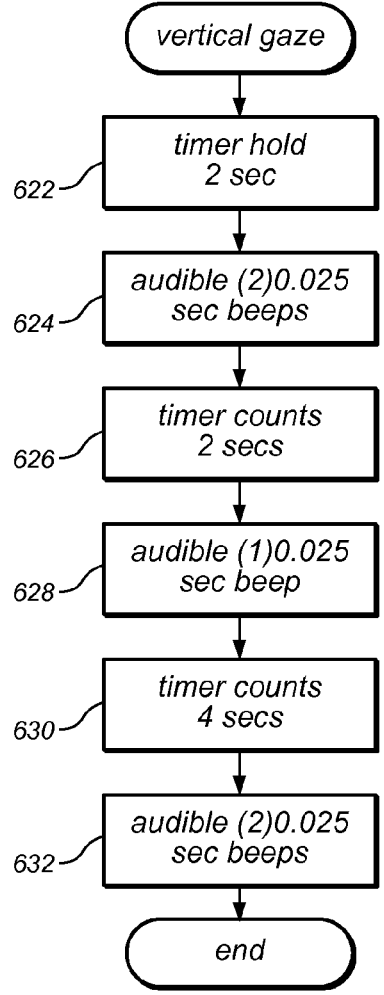
FIG. 6a
FIG. 6b

HANDHELD TELEPHONY DEVICE FOR FIELD SOBRIETY TESTING

PRIORITY INFORMATION

This application claims priority as a divisional of U.S. application Ser. No. 13/667,587, entitled "HANDHELD COMPUTING DEVICE FOR ADMINISTERING A GAZE NYSTAGMUS TEST," filed Nov. 2, 2012, which is a continuation of U.S. application Ser. No. 12/837,960 entitled "DEVICE FOR ADMINISTERING A GAZE NYSTAGMUS FIELD SOBRIETY TEST", filed Jul. 16, 2010, now U.S.Pat. No. 8,317,328 B1 which claims benefit of priority of U.S. provisional application Ser. No. 61/230,009 titled "Device for Testing of Horizontal and Vertical Gaze Nystagmus Field Sobriety Test", filed Jul. 30, 2009, whose inventors are Royger Paul Harris and Doyal Eugene Hobbs, all three of which are hereby incorporated by reference in their entirety as though fully and completely set forth herein and relied on for claim of priority.

FIELD OF THE INVENTION

The present invention relates to the field of testing and measurement, and more particularly to the field of diagnostic tests.

DESCRIPTION OF THE RELATED ART

Field sobriety tests are used by test administrators to assess the alcohol and narcotic impairment of test subjects. Frequently, test administrators are law enforcement or medical personnel and test subjects are suspects or patients. When properly administered and documented, field sobriety tests can be used to establish probable cause for an arrest or for a warrant to allow the gathering of evidence. Additionally, a properly administered and documented field sobriety test can be used as evidence at trial to support the guilt of a test subject with respect to an offense for which alcohol or narcotic impairment is a required element of the offense. Further, field sobriety tests can be used to assess the condition of a patient during initial medical triage.

Field sobriety tests include tests for horizontal and vertical gaze nystagmus. Gaze nystagmus refers to a jerking motion exhibited when the eye gazes to the side or upward. In the context of field sobriety tests, alcohol consumption or consumption of certain other central nervous system depressants, inhalants or phencyclidine, hinders the ability of the brain to correctly control eye muscles, therefore causing the jerk or bounce associated with gaze nystagmus.

Existing methods for conducting and documenting gaze nystagmus tests are subject to challenge with respect to the reliability of the administration and documentation of the test in the field. Specifically, defense attorneys frequently attempt to challenge the admissibility of the test or argue to the finder of fact that the results of the gaze nystagmus tests were tainted by improper administration and documentation. In the medical context, an improperly conducted gaze nystagmus test can lead to incorrect diagnosis and treatment decisions. Existing tools and methods for performing the gaze nystagmus tests do not provide adequate guarantees of complete compliance with standards for administering the test. Further, existing tools and methods for performing of the gaze nystagmus tests do not provide adequate guarantees of reliable recording and documentation of test results.

SUMMARY OF THE INVENTION

Various embodiments of a device for performing a gaze field sobriety test are disclosed.

In one embodiment, the device includes a housing. A light source is affixed in or on the housing. The light source generates light during at least a portion of the gaze field sobriety test. A speaker positioned in or on the housing generates sounds during at least a portion of the gaze field sobriety test. A power source is coupled to the speaker and the light source. An input is positioned on the housing. The input is selectable by a test administrator to initiate an indication at a predetermined time interval during at least a portion of the gaze field sobriety test. The indication may be an audible sound through the speaker, a visual indication such as light, a device vibration, or other type of indication. The indication (such as the audible sound) is provided to the test administrator during the gaze field sobriety test to assist in proper performance of the gaze field sobriety test. In one embodiment the device is a portable computing device, such as a smartphone, that is configured for use as an aid in performing the gaze filed sobriety test.

BRIEF DESCRIPTION OF THE DRAWINGS

A better understanding of the present invention can be obtained when the following detailed description of the preferred embodiment is considered in conjunction with the following drawings, in which:

FIGS. 6a-6b are block diagrams illustrating test patterns executed by a testing device in support of tests in accordance with an example embodiment of the present invention.

Figure 1A:
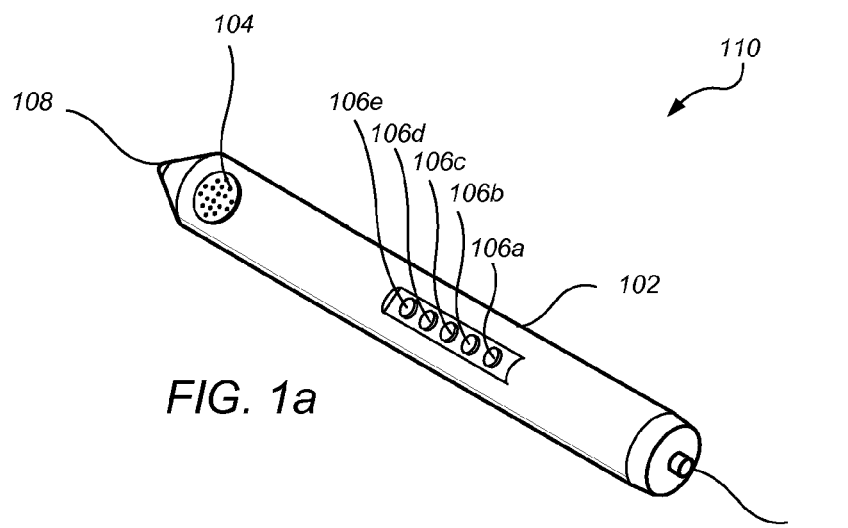
FIG. 1a illustrates a top view of a testing device in accordance with a first example embodiment of the present invention.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE EMBODIMENTS

Embodiments of the present invention provide a device to assist in performing a reliable and easily documentable gaze field sobriety test. The term "gaze field sobriety test" refers to any of various types of tests which involve assessing movement of a test subject's eyes as they attempt to follow a moving object. Thus the term "gaze field sobriety test" includes, but is not limited to, the various gaze nystagmus tests described herein. As discussed above, gaze field sobriety tests include tests for horizontal and vertical gaze nystagmus. Gaze nystagmus refers to a jerking motion exhibited when the eye gazes to the side or upward. Gaze nystagmus is detectable by observing a test subject's pupil as it follows a moving object.

Four gaze nystagmus tests are commonly administered. A first horizontal gaze nystagmus test is designed to allow observation of the lack of smooth pursuit as the eye follows the object moving along a horizontal line in front of a test subject. A test administrator conducts such a test by moving an object slowly but steadily from the center of the subject's face towards the left ear. The left eye should smoothly follow the object, but if the eye exhibits nystagmus, the test administrator notes the clue as an indication of intoxication. The test administrator then checks the right eye.

A second gaze nystagmus test is designed to allow observation of distinct and sustained nystagmus at maximum deviation of the eye from a center line of the test subject's view. Starting again from the center of the test subject's face, the test administrator moves the object toward the left ear, bringing the eye as far over as possible, and holds the object there for four seconds. The test administrator notes the clue if there is a distinct and sustained nystagmus at this point. The test administrator holds the object at maximum deviation for at least four seconds to ensure that quick movement of the object did not possibly cause the nystagmus. The test administrator then checks the right eye. This is also referred to as "end-point" nystagmus.

A third gaze nystagmus test is designed to allow observation of the onset of nystagmus prior to 45 degrees. The test administrator moves the object at a speed that would take about four seconds for the object to reach the edge of the test subject's left shoulder. The test administrator notes this clue if the point or angle at which the eye begins to display nystagmus is before the object reaches forty-five degrees from the center of the test subject's face. The test administrator then moves the object towards the test subject's right shoulder. Generally, forty-five degrees from center is at the point where the object is in front of the tip of the subject's shoulder. As a rule of thumb, a person's blood alcohol concentration can be estimated by subtracting the angle of onset from 50 degrees. Therefore, a person with an angle of onset of nystagmus at 35 degrees has a blood alcohol concentration of approximately 0.15%

A fourth common gaze nystagmus test is designed to allow observation of vertical nystagmus. In a vertical nystagmus test, the test administrator checks for vertical nystagmus by raising the object several inches above the subject's eyes. Vertical nystagmus is commonly interpreted as an indication of high doses of alcohol, other central nervous system (CNS) depressants or inhalants, and the consumption of the drug phencyclidine (PCP).

In each of the tests described above, existing methods for conducting and documenting gaze nystagmus tests are subject to challenge with respect to the reliability of the administration and documentation of the test in the field. Furthermore, the reliability of testing is important in the use of the gaze nystagmus test as a medical diagnostic technique.

Defense attorneys frequently attempt to challenge the admissibility of the test or argue to the finder of fact that the results of the gaze nystagmus tests were tainted by improper administration and documentation. Defense attorneys frequently argue that the moving object used during the test was moved too quickly, therefore causing a false positive result. In the medical diagnostic context, false positive results can lead to misdiagnosis and improper treatment decisions.

Embodiments of the present invention provide a standardized device used as a moving object in performing gaze nystagmus tests. The device may include a light source positioned in or on a housing, so that the test subject may follow the light generated by the light source during conduct of the test. In other embodiments, the device may comprise another visual indication for the test subject to follow, such as a fluorescent color on the device, etc. The device may also include a speaker positioned in or on the housing and configured to generate sounds. The sounds provide an indication to the test administrator of the passage of a particular amount of time. For instance, in the sustained nystagmus at maximum deviation, embodiments of the device may provide for auditory signals, e.g., four seconds apart, to ensure that the object was held in place for the amount of time needed to protect the results of the test from legal challenge. The device may also generate other types of indications to indicate the passage of a particular amount of time, such as a visual indication (light), device vibration, other indications, or some combination thereof. Additionally, in the "smooth pursuit" test, embodiments of the device may provide for indications (such as auditory signals) spaced over a fixed interval. These indications (or signals) can be taken as a cue to begin and end movement, thereby providing the test administrator with a reliable guide to the speed of object movement at which the test is to be conducted. By providing reliable measurement of time and cues to the passage of time in order to assure all interested parties that the test was conducted correctly, embodiments of the present invention may increase the reliability of test results and protect the results of the test from a legal challenge on the basis of an assertion that the object was moved in too short a time period.

In some embodiments of the present invention, additional features are included. These figures include an ink pen built into the housing of the device for recording test results. Some embodiments of the present invention may include an audio or video recording device for capturing test subject response to the test. Some embodiments include a gyroscopic motion sensor for monitoring the rate of movement of the device. A memory may be included on the device for storing audio/video captured during the test and/or for storing data from the motion sensor, which may be used to confirm proper administration of the test. Additionally, in some embodiments, additional auditory cues, such as instructions to the test administrator or test subject, can be provided, possibly in a plurality of languages. Some embodiments of the present invention will also include interface components to allow the upload and download of data. Finally, in some embodiments, the invention is embodied as a portable computing device, such as a smartphone.

With reference now to the figures, and specifically with reference to FIG. 1a, a top view of a testing device in accordance with a first example embodiment of the present invention is illustrated. A device 110 includes a light source 100, such as a light emitting diode (LED) attached to a housing 102. The light source 100 is used to enhance the visibility of the device and assist the test subject in focusing on the device. In one embodiment, the light source is of sufficient strength to allow the device to function as a flashlight. A speaker 104 is included and provides the audible signals, such as beeping sounds or spoken language instructions, for performing the test. A series of buttons 106a-e are provided as inputs for controlling operation of the device. The control schema employed in operating the device will vary between embodiments of the present invention. For instance, in one embodiment of the present invention, actuation of button 106a is used to activate or de-activate light source 100. In such an embodiment, each of buttons 106b-e is used to start or stop the audible signals associated with the performance of a different gaze nystagmus test. Patterns of sounds and time intervals between sounds used for performing several example tests are discussed below with respect to FIGS. 5a-6b.

In an alternative embodiment, actuation of button 106a is used to activate or de-activate light source 100, while button 106b is used to select a test (cycling through each of a series of different tests with each actuation of button 106b) and button 106c is used to select a language for providing test instructions (cycling through each of a series of spoken languages with each actuation of button 106c). In such an embodiment, actuation of button 106d is used to start the selected test in the selected language and button 106e is used to suspend any test activity. In the embodiment shown in FIG. 1a, an optional writing utensil 108 is provided for recording results of the test.

Figure 1B:
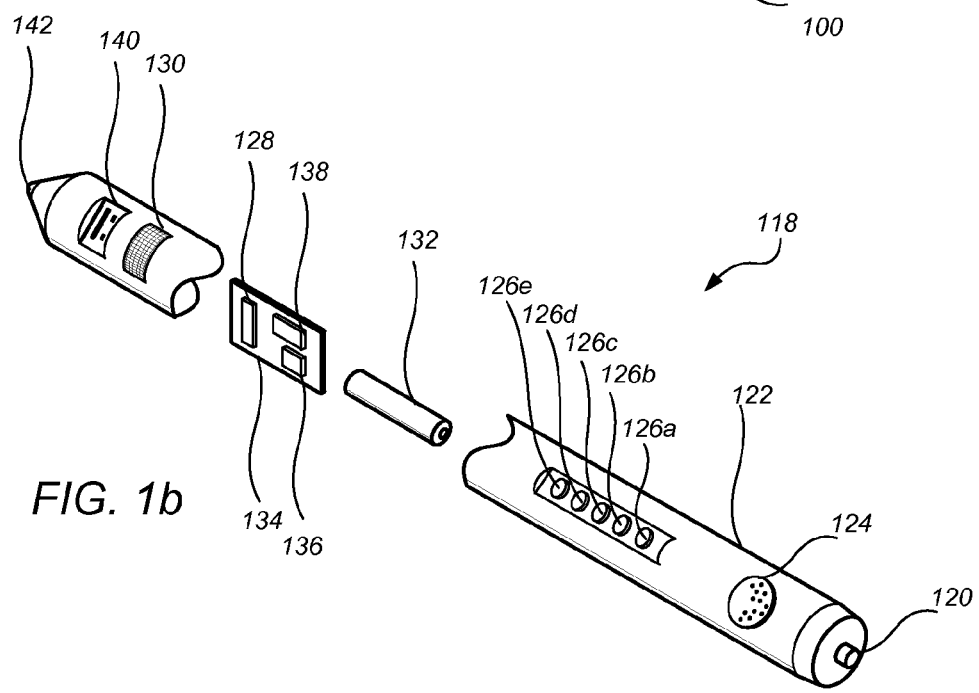
FIG. 1b illustrates a cutaway view of a testing device in accordance with a second example embodiment of the present invention.

Turning now to FIG. 1b, a cutaway view of a testing device in accordance with a second example embodiment of the present invention is depicted. A device 118 includes a light source 120, such as an LED attached to a housing 122. The light source 120 is used to enhance the visibility of the device and assist the test subject in focusing on the device. A speaker 124 is included and provides the audible signals, such as beeping sounds or spoken language instructions, for performing the test. A series of buttons 126a-e are provided as inputs for controlling operation of the device. The control schema employed in operating the device will vary between embodiments of the present invention.

In one embodiment, actuation of button 126a is used to activate or de-activate light source 120, while button 126b is used to select a test (cycling through each of a series of different tests with each actuation of button 126b) and button 126c is used to select a language for providing test instructions (cycling through each of a series of spoken languages with each actuation of button 126c). In such an embodiment, actuation of button 126d is used to start or stop the selected test in the selected language and button 126e is used to begin recording of both the motion of the device with an internal motion sensor 128 and sounds, such as those sounds recordable during the test, with a microphone 130.

In the embodiment shown in FIG. 1b, part of the housing is cut away to reveal internal components. The internal components include a power source 132, such as a battery. The internal components also include a circuit board 134 for interconnecting components of the device. Mounted on circuit board 134 is a memory 136 for storing program instructions that are executable to enable the device to perform the functions described herein. The memory 136 may also store data, such as sounds provided over speaker 124 and data recorded by motion sensor 128 and microphone 130. Motion sensor 128 is also mounted on circuit board 134. A processor 138 may execute the program instructions stored in the memory 136 to control and execute various functions of the device and is mounted on circuit board 134. An I/O adapter 140, such as a USB adapter, is provided for receiving data into memory 136 and transmitting data stored in memory 136. The I/O adapter may also be used to update the program instructions in the memory 136, e.g., to allow for updated or new gaze field sobriety tests performed by the device. In some embodiments, a radio frequency adapter, such as a Bluetooth™ unit, may be substituted for a USB adapter. In the embodiment shown in FIG. 1b, an optional writing utensil 142 is provided for recording results of the test.

Figure 1C:
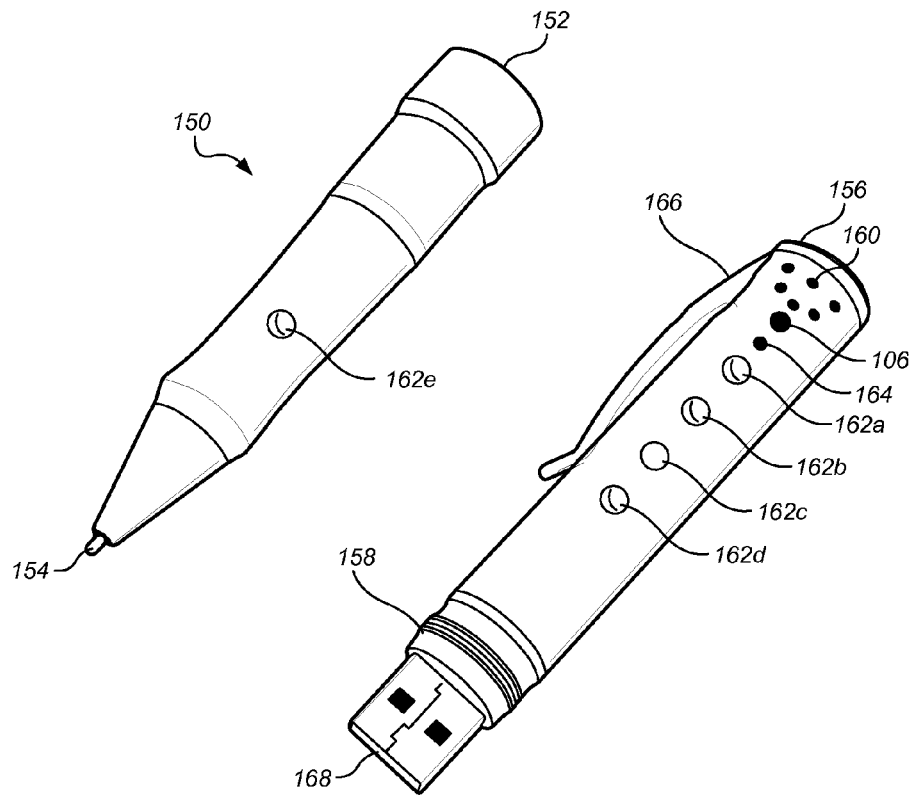
FIG. 1c is a top view of an alternative embodiment of a testing device in accordance with a third example embodiment of the present invention.

With reference now to FIG. 1c, a top view of a third embodiment of a testing device in accordance with an example embodiment of the present invention is presented. A device 150 separates into a lower housing portion 152 and an upper housing portion 156. Lower housing portion 152 contains a light source 154, such as an LED. Threads 158 on upper housing portion 156 allow for removably fixed attachment of lower housing portion 152 (by means of complimentary threads within lower housing portion 152, which are not visible in the diagram) to upper housing portion 156. The light source 154 is used to enhance the visibility of the device and assist the test subject in focusing on the device. In an embodiment such as FIG. 1c, multiple power sources (not shown) may be provided, one in each of lower housing 152 and the upper housing 156.

Upper housing portion 156 contains a speaker 160 that provides audible signals, such as beeping sounds or spoken language instructions, for performing the test. A series of buttons 162a-e are provided as inputs for controlling operation of the device. The control schema employed in operating the device will vary between embodiments of the present invention.

In one embodiment, actuation of button 162e is used to activate or de-activate light source 154, while button 126d is used to select a test (cycling through each of a series of different tests with each actuation of button 126d) and button 126c is used to select a language for providing test instructions (cycling through each of a series of spoken languages with each actuation of button 126c). In such an embodiment, actuation of button 126b is used to start or stop the selected test in the selected language and button 126a is used to begin recording of the motion of the device with an internal gyroscopic motion sensor (not shown) and sounds recordable during the test with a microphone 164. A clip 166 is provided for affixing device 150 to a pocket, a belt or other surface. An I/O adapter 168, such as a USB connection, is provided receiving data into memory and transmitting data stored in memory.

Figure 2:
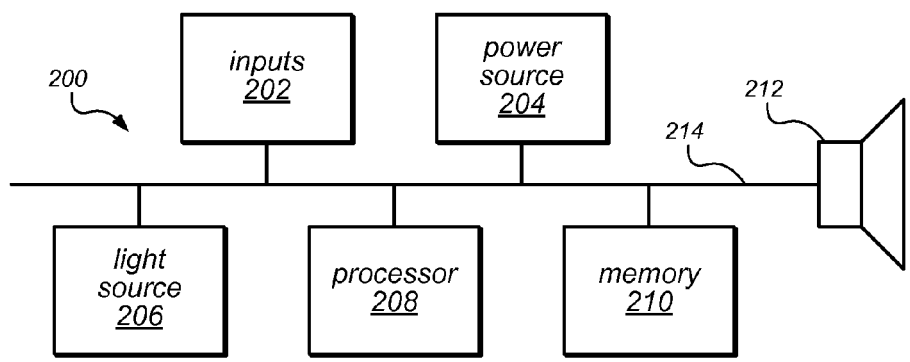
FIG. 2 illustrates a schematic view of a testing device in accordance with an example embodiment of the present invention.

Turning now to FIG. 2, a schematic view of a testing device in accordance with an example embodiment of the present invention is presented. Device 200 includes a central interconnect 214, such as a circuit board or wires. Central interconnect provides for connections among inputs 202, a power source 204, a light source 206, a processor 208, and a memory 210. Inputs 202 can include buttons (such as buttons 162a-e of FIG. 1c), an I/O adapter (such as I/O adapter 168 of FIG. 1c), a microphone (such as microphone 160 of FIG. 1c), a camera (such as camera 316 of FIG. 3, which is discussed below), an R/F unit (such as transceiver 302 of FIG. 3, which is discussed below), and a motion sensor (such as motion sensor 128 of FIG. 1b). Power source 204 may be embodied as one or more disposable batteries, or optionally, the combination of a rechargeable battery and a transformer or solar cells for receiving power. Light source 206 may include an LED, a light bulb, or other means for generating light.

Additionally, in some embodiments, a light source capable of emitting light of varying colors may be used, such as to emit white light while performing a test, a green light to indicate that a test was properly administered, and a red light to indicate a failure of test administration due to improper device movement. For example, a motion sensor (such as a gyroscope) may record the motion of the device during the test, wherein the motion is recorded with respect to time. A software program executing on the device may use this recorded motion in conjunction with the timing of the auditory signals to provide an indication of whether or not the test was performed properly. For example, the software program may determine whether the device was moved too quickly relative to the timing of the auditory and/or visual signals indicating to the test administrator when to halt and reverse motion of the device, etc. The device may then provide an immediate audial or visual indication as to whether or not the test was performed properly. This immediate indication is important, because if the device indicates that the test was not performed properly, the test administrator can immediately re-perform the test. If the device indicates that the test was performed properly, this can be admissible at trial of proof of proper performance of the test.

Processor 208 can be provided to control the operation of device 200. As used herein, a processor can include a programmable processor, such as a microcontroller, central processing unit (CPU), etc., or an application-specific integrated circuit (ASIC) or programmable logic array (PLA), such as a field programmable gate array (FPGA), designed to implement the functions performed by the device, such as control, data capture, and sound output. Memory 210 can be used to store data and instructions. Speaker 212 provides audible output from the device.

Figure 3:
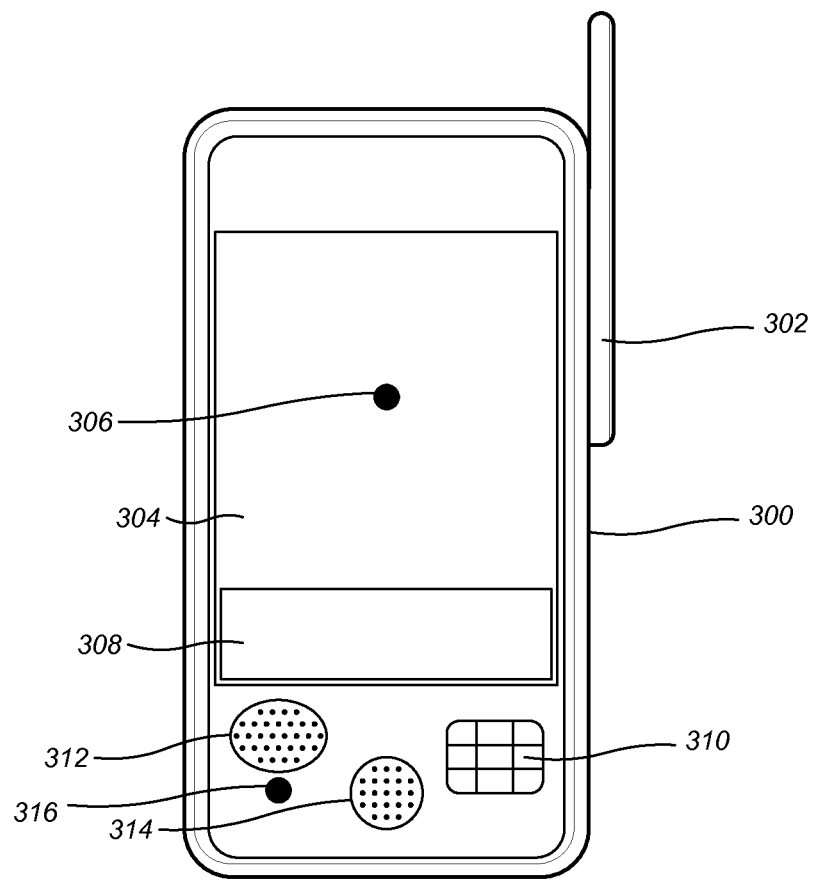
FIG. 3 illustrates a mobile computing device configured for use as a testing device in accordance with an example embodiment of the present invention.

Referring now to FIG. 3, a mobile computing device configured for use as a testing device in accordance with an example embodiment of the present invention is illustrated. Mobile computing device 300 may be any of various types of devices. For example, mobile computing device 300 may be a smartphone, such as an IPHONE™, ANDROID™ phone, Blackberry, etc. Mobile computing device 300 may also be another type of portable computer, such as a tablet PC, e.g., and iPAD. Mobile computing device 300 may include a radio frequency transceiver 302. In some embodiments, radio frequency transceiver 302 communicates with a telephony network and/or with 802.11(x) networks.

A screen 304 can be used as a light source by activating an illuminated pixel group 306 on the screen. In some embodiments, screen 304 is a touch screen and device controls 308 are provided as renderings of buttons on screen 304 for use as inputs. In other embodiments, buttons 310 can be provided as device controls for use as inputs during test administration.

In some embodiments of the present invention, such as mobile computing devices with very large screens, the mobile computing device is held stationary and the illuminated pixel group 306 is moved to provide the moving object used in performing the field sobriety test.

A speaker 312 is provided for generating audible signals. A microphone 314 and a front-facing camera 316 (e.g., as available in iPHONE 4) are provided for recording sounds and still images/video generated by a test subject. Images of a test subject, including recording still images or video of the subject's eyes, may be used as later proof of whether the test subject passed the gaze field sobriety test.

As will be apparent to one of skill in the art after having read the present disclosure, the embodiments of the present invention discussed herein each include optional features of the present invention, and embodiments of the present invention may be practiced without those optional features or with the addition of features that are not shown. Additionally, each of the embodiments of the present invention depicted in FIGS. 1a-3 may include features and parts that one skilled in the art to which the invention pertains will know to include in the manufacture and use of such an embodiment, but which are omitted for clarify of the diagrams and succinctness of the discussions in this disclosure.

It is noted that current smartphones, such as the IPHONE 4, provide the various hardware capabilities required, including a processor, memory, a display (which can be used as both a light source and a graphical user interface in place of buttons 106a-106e), a microphone, speakers, front facing camera, motion sensor, and a communications interface. Thus in one embodiment a software application is created, such as an IPHONE application or ANDROID application, which configures an existing smartphone to perform the operations described herein. For example, such an IPHONE application for conducting a gaze field sobriety test may be made available on the APPLE App Store for downloading by various IPHONE users.

Figure 4A:
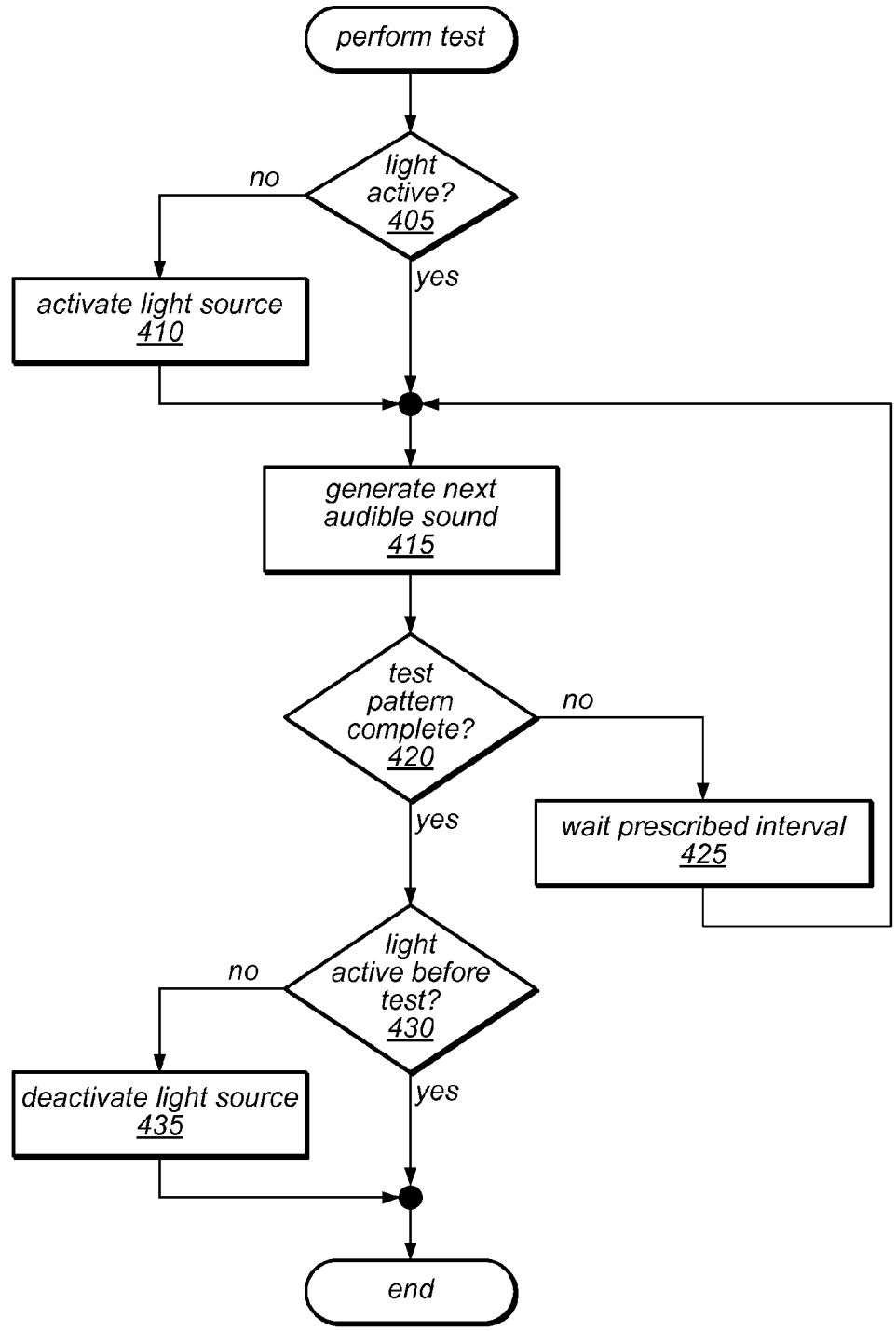
FIG. 4a is a block diagram illustrating functions performed by a testing device in support of a test in accordance with an example embodiment of the present invention.

Turning now to FIG. 4a, a flowchart diagram illustrating functions performed by a testing device in support of a test in accordance with an example embodiment of the present invention is illustrated. In response to an input, such as pressing a button, the device performs actions associated with a selected gaze nystagmus test.

A determination is made as to whether a light source on the device is activated (step 405). If the light source has not been activated, the device activates its light source (step 410).

An indication, such as an audible sound, visual indication, etc. is generated (step 415) to indicate to indicate the beginning or end of a portion of a test. In some embodiments of the present invention, the audible sound is a simple tone (beeping noise). In other embodiments, the audible sound can include spoken instructions to either the test administrator or the test subject. In some embodiments of the present invention, the spoken instructions are available in a series of different languages. In some embodiments, instead of an audible sound, the light source flashes or is otherwise modified to indicate the beginning or end of a portion of the test. Alternatively, the device may vibrate to indicate the beginning or end of a portion of the test.

Once the indication (e.g., audible sound) is generated to indicate the beginning of the test, the test administrator may then move the device in a desired direction in front of the test subject, while observing the eyes of the test subject. For example, the test administrator may move the device left, right, up or down, wherein the test subject has been previously requested to follow the device with his/her eyes. After the test administrator has moved the device a period of time, e.g., 4 seconds, an indication, such as an audible sound, visual indication (such as a flash of light), device vibration, etc., may be generated by the device to indicate that the test administrator should halt movement of the device and reverse the direction of the device, i.e., move the device in the opposite direction. This second indication (e.g., audible sound, visual indication, vibration, etc.) alerts the test administrator of the appropriate time to halt and reverse movement of the device, and thus provides increased accuracy and conformity of the gaze field sobriety test. This provides a greater likelihood that the test administrator will conduct the test properly, and hence make it more likely that the conducted test will hold up in court. Various test patterns for sample gaze nystagmus tests are discussed below with respect to FIGS. 5a-6b.

A determination is then made as to whether a test pattern associated with the selected test has been completed (step 420).

If the test pattern has not been completed, then the device waits a prescribed interval (step 425), which depends on the test pattern, before returning to step 415, which is described above. If the test pattern is complete, a determination is made as to whether the light source was active before initiation of the test (step 430). If the light source was not active before the initiation of the test, the light source is de-activated (step 435). The process then ends.

Figure 4B:
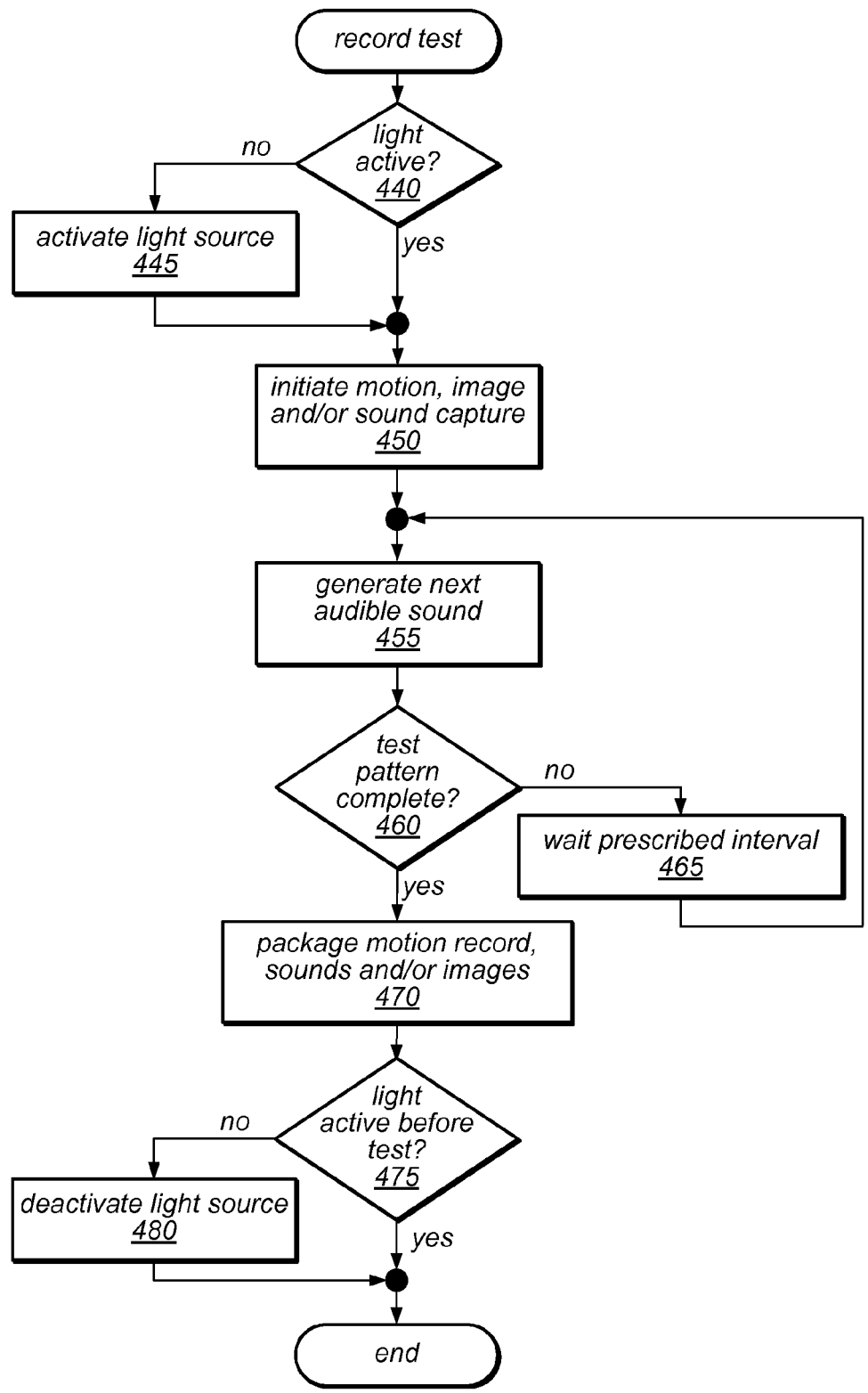
FIG. 4b is a block diagram illustrating functions performed by a testing device in support of and while recording a test in accordance with an example embodiment of the present invention.

With reference now to FIG. 4b, a flowchart diagram illustrating functions performed by a testing device in support of and while recording a test in accordance with an example embodiment of the present invention is depicted.

In response to an input, such as pressing a button, the device performs actions associated with a selected gaze nystagmus test.

A determination is made as to whether a light source on the device is activated (step 440). If the light source has not been activated, the device activates the light source (step 445).

Capture of data from any of a camera, a microphone and a motion sensor is then initiated (step 450).

An audible sound (or visual indication or device vibration or other type of indication) is generated (step 455) to indicate to indicate the beginning or end of a portion of a test. In some embodiments of the present invention, the audible sound is a simple tone (beeping noise). In other embodiments, the audible sound can include spoken instructions to either the test administrator or the test subject. In some embodiments of the present invention, the spoken instructions are available in a series of different languages. It is noted that steps 450 and 455 may be performed in either order, or may be performed simultaneously. In other words, the audible sound or other indication in 455 may occur concurrently with the device beginning to record/capture data.

As described above with respect to FIG. 4a, once the indication (e.g., audible sound) is generated to indicate the beginning of the test, the test administrator may then move the device in a desired direction in front of the test subject, while observing the eyes of the test subject. For example, the test administrator may move the device left, right, up or down, wherein the test subject has been previously requested to follow the device with his/her eyes. After the test administrator has moved the device a period of time, e.g., 4 seconds, an indication (e.g., such as an audible sound, a visual indication such as a flash of light, a device vibration, or other indication) may be generated by the device to indicate that the test administrator should halt movement of the device and reverse the direction of the device, i.e., move the device in the opposite direction. This second indication alerts the test administrator of the appropriate time to halt and reverse movement of the device, and thus provides increased accuracy and conformity of the gaze field sobriety test. This provides a greater likelihood that the test administrator will conduct the test properly, and hence make it more likely that the conducted test will hold up in court.

During the time when the test administrator is moving the device to conduct the gaze field sobriety test, the device may capture various data during the test. For example, a camera on the front of the device may record video of the user's eyes during the test. The combination of a light sensor associated with a camera and the light source may further be used to measure the distance between the device and the subject's face. Additionally, distance to the face of the test subject may be subsequently calculated by comparing the recorded distance between photographed features of the face of the test subject to subsequent measurements of the face of the subject. Also, a microphone on the device may record any words spoken by the test subject during the test. Further, in one embodiment, a motion sensor on the device (such as a gyroscope) may record motion of the device, including the direction in which the device is moved, how fast and how far it is moved, and for how long the device is moved before motion is halted and the movement direction is reversed. This motion data may be stored on the device as later proof that the test was conducted in a proper manner. Some embodiments may record a verification of angular movement with respect to the test subject's face, for example using the combination of motion data described above and distance measurements described above, which is useful in recording angle of nystagmus onset.

In addition, in one embodiment during some portion during (or before or after) the test, a GPS unit on the device may record the GPS coordinates of where the test was administered, in case there is any dispute as to the specific location where the test was actually administered.

A determination is then made as to whether a test pattern associated with the selected test has been completed (step 460). Various test patterns for sample gaze nystagmus tests are discussed below with respect to FIGS. 5a-6b.

If the test pattern has not been completed, then the device waits a prescribed interval (step 465), which depends on the test pattern, before returning to step 455, which is described above. If the test pattern is complete, any available motion records, sounds, and images are packaged in one or more exportable data structures (step 470). A determination is made as to whether the light source was active before initiation of the test (step 475). If the light source was not active before the initiation of the test, the light source is de-activated (step 480). The process then ends.

The method of FIG. 4b may be implemented by the device shown in FIGS. 1a-c, or by the mobile computing device of FIG. 3. It is noted that where the method is performed by a mobile computing device, existing smartphones currently include the various functionality required to implement the method of FIG. 4b.

As will be apparent to one of skill in the art after having read the present disclosure, embodiments of the present invention may be practiced with various other optional features or with the addition of steps that are not shown. Additionally, each of the embodiments of the present invention depicted in FIGS. 4a-4b may include operations that one skilled in the art to which the invention pertains will know to include in the practice of such an embodiment, but which are omitted for clarity of the diagrams and succinctness of the discussions in this disclosure.

FIGS. 4a-4b have provided examples of processes performed by the current device in support of gaze nystagmus tests. In steps 415-420 of FIG. 4a and steps 455-465 of FIG. 4b, test patterns are executed through a series of sound emissions and delays between the sound emissions. The relationships between those sound emissions and delays and various gaze nystagmus tests are explained below in terms of gaze nystagmus test patterns with respect to FIGS. 5a-6b.

Figure 5A:
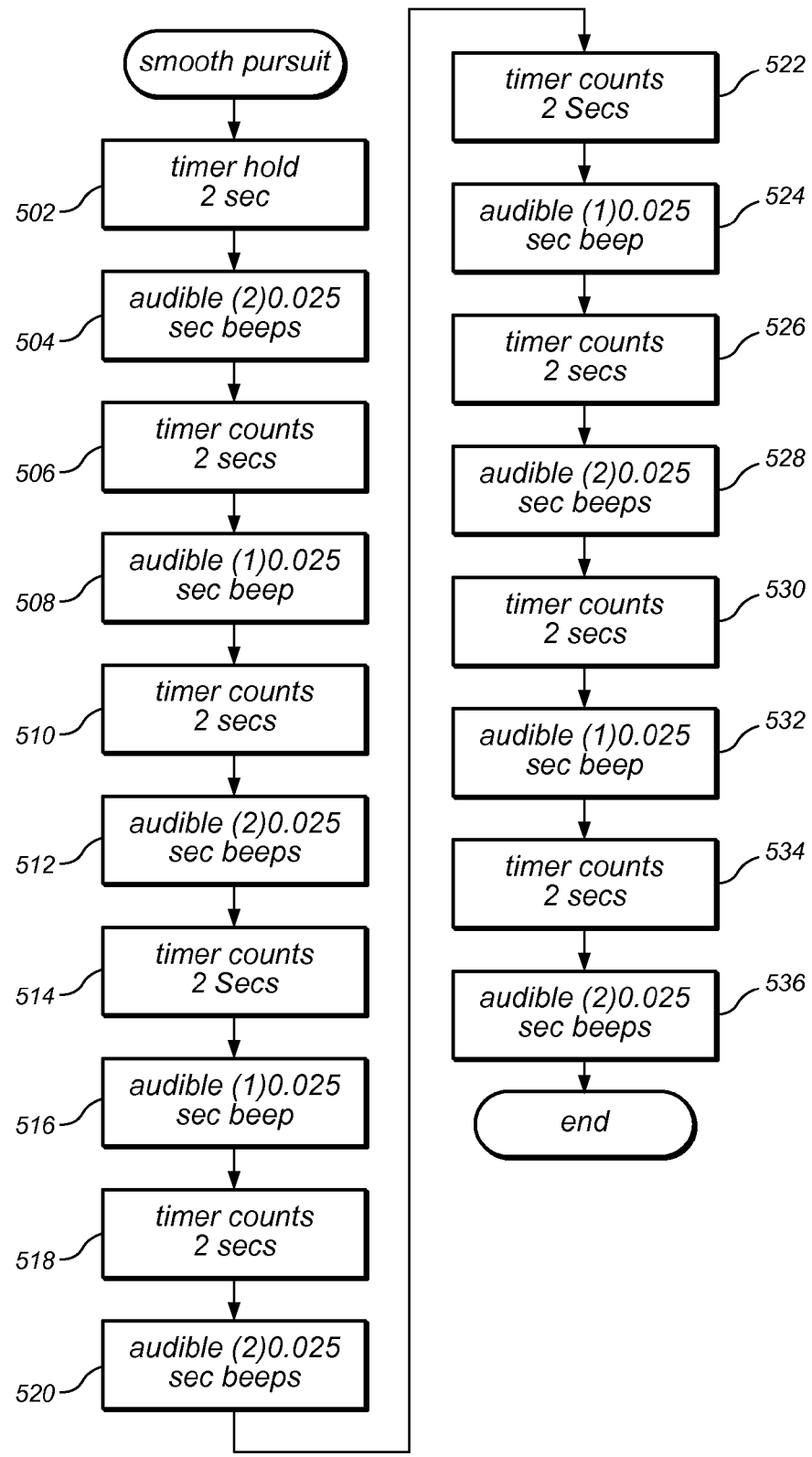
FIGS. 5a-5b are block diagrams illustrating test patterns executed by a testing device in support of tests in accordance with an example embodiment of the present invention.

Referring now to FIG. 5a, a block diagram illustrating a test pattern executed by a testing device in support of a smooth pursuit horizontal gaze nystagmus test in accordance with an example embodiment of the present invention is illustrated. In response to initiation of the test, a timer executes a two second hold (step 502). The device then emits a pair of audible 0.025-second beeping sounds (step 504). After this signal, a timer counts off two seconds, during which time the test administrator will move the device from a position directly in front of the test subject to a position in front of and to the right side of the test subject such that the subject's eyes follow the device as far as they can to the side (step 506). The test administrator notes whether the eyes of the test subject follow the device smoothly or jerk from nystagmus. An audible 0.025-second beep is then emitted (step 508). After this signal, a timer counts off two seconds, during which time the test administrator reverses direction and moves the device from the position in front of and to the side of the test subject and back to the position directly in front of the test subject (step 510). The test administrator notes whether the eyes of the test subject follow the device smoothly or jerk from nystagmus.

The device then emits a pair of audible 0.025-second beeping sounds (step 512). After this signal, a timer counts off two seconds, during which time the test administrator will move the device from a position directly in front of the test subject to a position in front of and to the left side of the test subject such that the subject's eyes follow the device as far as they can to the side (step 514). The test administrator notes whether the eyes of the test subject follow the device smoothly or jerk from nystagmus. An audible 0.025-second beep is then emitted (step 516). After this signal, a timer counts off two seconds, during which time the test administrator reverses direction and moves the device from the side of the position in front of and to the left side of the test subject and back to the position directly in front of the test subject (step 518). The test administrator notes whether the eyes of the test subject follow the device smoothly or jerk from nystagmus.

The test is then repeated. The device then emits a pair of audible 0.025-second beeping sounds (step 520). After this signal, a timer counts off two seconds, during which time the test administrator will move the device from a position directly in front of the test subject to a position in front of and to the right side of the test subject such that the subject's eyes follow the device as far as they can to the side (step 522). The test administrator notes whether the eyes of the test subject follow the device smoothly or jerk from nystagmus. An audible 0.025-second beep is then emitted (step 524). After this signal, a timer counts off two seconds, during which time the test administrator reverses direction and moves the device from the position in front of and to the right side of the test subject and back to the position directly in front of the test subject (step 526). The test administrator notes whether the eyes of the test subject follow the device smoothly or jerk from nystagmus.

The device then emits a pair of audible 0.025-second beeping sounds (step 528). After this signal, a timer counts off two seconds, during which time the test administrator will move the device from a position directly in front of the test subject to a position in front of and to the left side of the test subject such that the subject's eyes follow the device as far as they can to the side (step 530). The test administrator notes whether the eyes of the test subject follow the device smoothly or jerk from nystagmus. An audible 0.025-second beep is then emitted (step 532). After this signal, a timer counts off two seconds, during which time the test administrator reverses direction and moves the device from the position in front of and to the left side of the test subject and back to the position directly in front of the test subject (step 534). The test administrator notes whether the eyes of the test subject follow the device smoothly or jerk from nystagmus. The device then emits a pair of audible 0.025-second beeping sounds (step 536) to signal the end of the test.

In an alternative embodiment, the device may replace or augment with instructional recordings the audible beeping indicated in FIGS. 5a-6b. For instance, recordings can be provided to explain the tests of FIGS. 5a-6b (or other tests used with the device) to the test subject. An example of such an instructional recording would include a recording at step 504, stating, "Your eyes are now going to be examined. Keep your head still and follow the illuminated stimulus device with your eyes only. Keep focusing on this stimulus until instructed to stop." Similar instructions can be provided with respect to the example tests described below with respect to FIGS. 5b-6b. For example, with respect to FIG. 5b, another example instruction could say, at step 544 (described below), "Maintain focus on the stationary stimulus device until instructed to do otherwise." Additionally, in some alternative embodiments, instructions to the test administrator may be provided in place of or in addition to beeping noises. For example, the audible 2-second beep of step 504 may be replaced with recorded instructions reminding the test administrator to perform the indicated movement. Such audio recordings may be provided in a plurality of languages, including English and Spanish, etc.

In some embodiments, a gyroscopic motion sensor may record the movements of the device. For instance, with respect to FIG. 5a, recording of movements can be used to ensure that the rate of device movement did not exceed an acceptable maximum rate of movement. Similarly, in the test described below with respect to FIG. 5b, recording of movements can be used to ensure the device was held in place for an appropriate length of time. In such embodiments, the light source on the device may indicate a successful test by providing an alternative sound pattern at step 520 or step 536 (for example, 3 beeping sounds for test failure or two beeping sounds for success). Alternatively, the color of light emitted at the light source could change (for example, to green for success or red for failure) at step 520 or step 536 or an audible recording such as "test successful" or "test failed, please repeat" could be emitted from the speaker. In alternative embodiments, a screen may be used to simulate the movement of a light source by altering the arrangement of lighted and darkened pixels. The test administrator will observe the test subject's eyes to ascertain whether the eyes follow the device smoothly. In alternative embodiments, a camera may be used to record the subject's eye movement during the test.

Figure 5B:
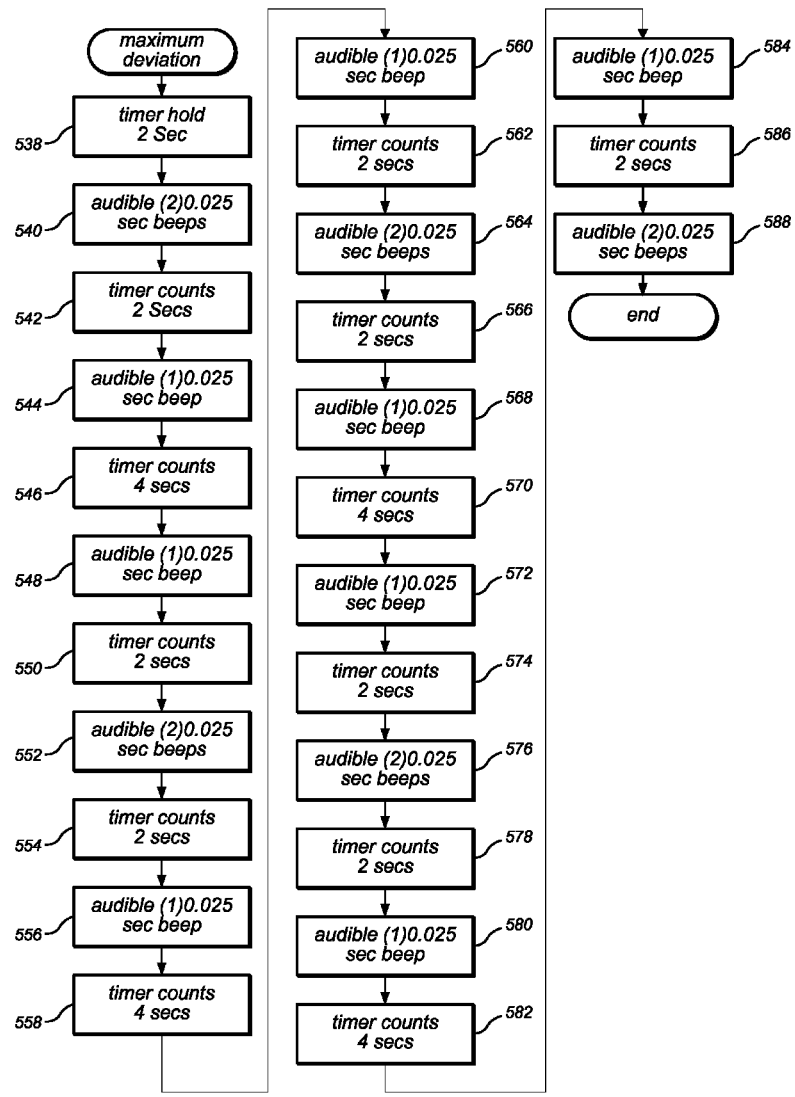

Turning now to FIG. 5b, a block diagram illustrating a test pattern executed by a testing device in support of a maximum deviation horizontal gaze nystagmus test in accordance with an example embodiment of the present invention is depicted. In response to initiation of the test, a timer executes a two second hold (step 538). The device then emits a pair of audible 0.025-second beeping sounds (step 540). After this signal, a timer counts off two seconds, during which time the test administrator will move the device from a position directly in front of the test subject to a position in front of and to the right side of the test subject such that the subject's eyes follow the device as far as they can to the right side (step 542). An audible 0.025-second beep is then emitted (step 544). A timer then counts four seconds (step 546). During this time, the test administrator observes whether the test subject's eyes exhibit nystagmus at maximum deviation. An audible 0.025-second beep is then emitted (step 548). After this signal, a timer counts off two seconds, during which time the test administrator reverses direction and moves the device from the side of the position in front of and to the side of the test subject to the position directly in front of the test subject (step 550).

The device then emits a pair of audible 0.025-second beeping sounds (step 552). After this signal, a timer counts off two seconds, during which time the test administrator will move the device from a position directly in front of the test subject to a position in front of and to the left side of the test subject such that the subject's eyes follow the device as far as they can to the left side (step 554). An audible 0.025-second beep is then emitted (step 556). A timer then counts four seconds (step 558). During this time, the test administrator observes whether the test subject's eyes exhibit nystagmus at maximum deviation. An audible 0.025-second beep is then emitted (step 560). After this signal, a timer counts off two seconds, during which time the test administrator reverses direction and moves the device from the position in front of and to the left side of the test subject to the position directly in front of the test subject (step 562).

The test is then repeated. The device then emits a pair of audible 0.025-second beeping sounds (step 564). After this signal, a timer counts off two seconds, during which time the test administrator will move the device from a position directly in front of the test subject to a position in front of and to the right side of the test subject such that the subject's eyes follow the device as far as they can to the right side (step 566). An audible 0.025-second beep is then emitted (step 568). A timer then counts four seconds (step 570). During this time, the test administrator observes whether the test subject's eyes exhibit nystagmus at maximum deviation. An audible 0.025-second beep is then emitted (step 572). After this signal, a timer counts off two seconds, during which time the test administrator reverses direction and moves the device from the position in front of and to the right side of the test subject to the position directly in front of the test subject (step 574).

The device then emits a pair of audible 0.025-second beeping sounds (step 576). After this signal, a timer counts off two seconds, during which time the test administrator will move the device from a position directly in front of the test subject to a position in front of and to the left side of the test subject such that the subject's eyes follow the device as far as they can to the left side (step 578). An audible 0.025-second beep is then emitted (step 580). A timer then counts four seconds (step 582). During this time, the test administrator observes whether the test subject's eyes exhibit nystagmus at maximum deviation. An audible 0.025-second beep is then emitted (step 584). After this signal, a timer counts off two seconds, during which time the test administrator reverses direction and moves the device from the position in front of and to the left side of the test subject to the position directly in front of the test subject (step 586). The device then emits a pair of audible 0.025-second beeping sounds (step 588) to signal the end of the test.

Referring now to FIG. 6a, a block diagram illustrating a test pattern executed by a testing device in support of a nystagmus angle-of-onset test in accordance with an example embodiment of the present invention is illustrated. In response to initiation of the test, a timer executes a two second hold (step 602). The device then emits a pair of audible 0.025-second beeping sounds (step 604). After this signal, a timer counts off one second, during which time the test administrator will move the device from a position directly in front of the test subject to a position in front of and to the right side of the test subject such that the subject's eyes follow the device as far as they can to the right side (step 606). An audible 0.025-second beep is then emitted (step 608). A timer then counts one second (step 610). During this time, the test administrator reverses direction and moves the device from the position in front of and to the right side of the test subject to the position directly in front of the test subject.

The device then emits an audible 0.025-second beep (step 612). After this signal, a timer counts off one second, during which time the test administrator will move the device from a position directly in front of the test subject to a position in front of and to the left side of the test subject such that the subject's eyes follow the device as far as they can to the left side (step 614). An audible 0.025-second beep is then emitted (step 616). A timer then counts one second (step 618). During this time, the test administrator reverses direction and moves the device from the position in front of and to the left side of the test subject to the position directly in front of the test subject. The device then emits a pair of audible 0.025-second beeping sounds (step 620) to signal the end of the test.

Turning now to FIG. 6b, a block diagram illustrating a test pattern executed by a testing device in support of a vertical gaze nystagmus test in accordance with an example embodiment of the present invention is depicted. In response to initiation of the test, a timer executes a two second hold (step 622). The device then emits a pair of audible 0.025-second beeping sounds (step 624). After this signal, a timer counts off two seconds, during which time the test administrator will move the device from a position directly in front of the test subject to a position in front of and above the test subject such that the subject's eyes follow the device as far as they can upward (step 626). An audible 0.025-second beep is then emitted (step 628). A timer then counts four seconds (step 630). During this time, the test administrator reverses direction and moves the device from the position above and in front of the test subject to the position directly in front of the test subject. The device then emits an audible 0.025-second beep (step 632) to signal the end of the test.

Figure 7:
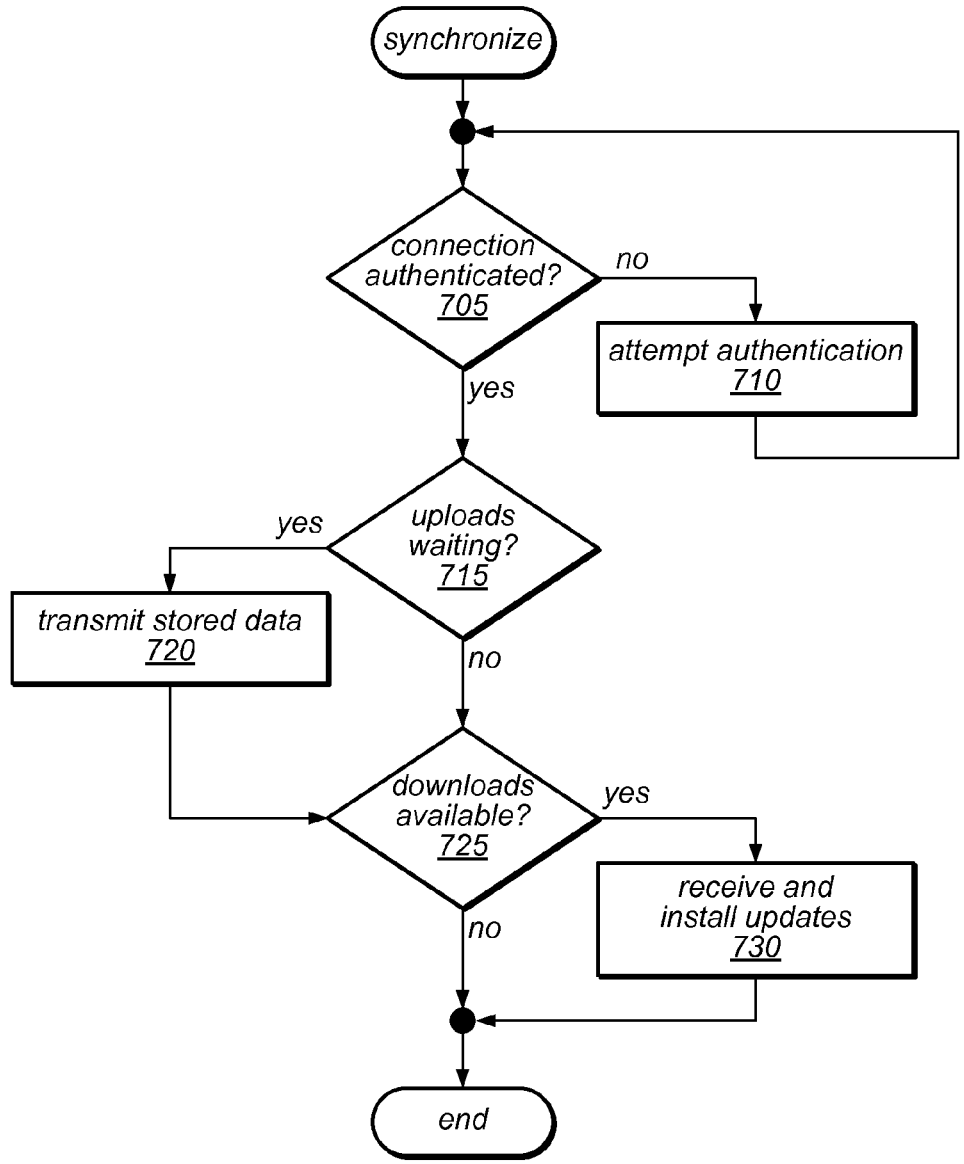
FIG. 7 is a block diagram illustrating functions performed by a testing device in sending and receiving test and instruction data in accordance with an example embodiment of the present invention.

Referring now to FIG. 7, a block diagram illustrating functions performed by a testing device in sending and receiving test and instruction data in accordance with an example embodiment of the present invention is illustrated. A determination is made as to whether a connection has been authenticated (for example, across a peripheral adapter such as USB adapter 168 of FIG. 1c or across a network using a wireless network adapter such as radio frequency transceiver 302) (step 705). If a connection has not been authenticated, the device attempts authentication of the connection (step 710). The process then returns to step 705, which is described above. If a connection has been authenticated, then a determination is made as to whether data is waiting in memory for performance of an upload (step 715). If data stored in memory is waiting to be uploaded, the stored data is transmitted to the external device with which the connection has been authenticated (step 720). A determination is made as to whether downloads for the device are available. If downloads are available, updates are received and installed. The updates can included sound files such as audible instructions for use in performing a gaze nystagmus test or internal instructions for programming the device. The process then ends.

As explained above, embodiments of the present invention provides tools for reliably conducting and documenting gaze nystagmus tests to reduce challenges to the reliability of the administration and documentation of the test in the field. The present invention provides enhanced indicia of compliance with standards for administering the test. Further, the present invention provides new tools for reliable recording and documentation of test results.

Although the embodiments above have been described in considerable detail, numerous variations and modifications will become apparent to those skilled in the art once the above disclosure is fully appreciated. It is intended that the following claims be interpreted to embrace all such variations and modifications.

We claim:

1. A mobile telephony device configured for use in performing a field sobriety test, wherein the device comprises:
 a housing;

a radio frequency transceiver for communicating with a wireless telephony network;
an antenna for performing wireless communications with the wireless telephony network;
a processor comprised in the housing;
a non-transitory memory medium comprised in the housing, wherein the memory medium stores program instructions executable to implement the field sobriety test;
a display screen positioned in or on the housing and configured to generate at least one test administrator signal during operation of the field sobriety test.

2. The mobile telephony device of claim 1, further comprising:
a speaker positioned in or on the housing and configured to generate sounds as prompts for conducting at least a portion of the field sobriety test.

3. The mobile telephony device of claim 1, further comprising;
a speaker positioned in or on the housing and configured to generate spoken instructions for conducting the field sobriety test.

4. The mobile telephony device of claim 1,
wherein the display screen is configured to act as a light source during at least a portion of the field sobriety test.

5. The mobile telephony device of claim 1, further comprising:
a motion sensor for recording movements of the mobile telephony device during the field sobriety test.

6. The mobile telephony device of claim 1, further comprising:
a video camera for recording a video of eye movements of a test subject during the field sobriety test.

7. The mobile telephony device of claim 1, further comprising:
a microphone for recording sounds during the field sobriety test.

8. A mobile telephony device configured for use in performing a field sobriety test, wherein the device comprises:
a housing;
a processor comprised in the housing;
a non-transitory memory medium comprised in the housing, wherein the memory medium stores program instructions executable to implement the field sobriety test;
a display screen positioned in or on the housing and configured to generate at least one test administrator signal during operation of the field sobriety test.

9. The mobile telephony device of claim 8, further comprising:
a speaker positioned in or on the housing and configured to generate sounds as prompts for conducting at least a portion of the field sobriety test.

10. The mobile telephony device of claim 8, further comprising;
a speaker positioned in or on the housing and configured to generate spoken instructions for conducting the field sobriety test.

11. The mobile telephony device of claim 8,
wherein the display screen is configured to act as a light source during at least a portion of the field sobriety test.

12. The mobile telephony device of claim 8, further comprising:
a motion sensor for recording movements of the mobile telephony device during the field sobriety test.

13. The mobile telephony device of claim 8, further comprising:
a video camera for recording a video of eye movements of a test subject during the field sobriety test.

14. The mobile telephony device of claim 8, further comprising:
a microphone for recording sounds during the field sobriety test.

15. The mobile telephony device of claim 8, wherein the program instructions executable to implement the field sobriety test comprise program instructions computer executable to implement:
providing a visual target on a handheld computing device, wherein
the visual target is provided during at least a portion of a gaze nystagmus test; and
generating at least one test administrator signal from the handheld computing device, wherein
the at least one test administrator signal provides an indication to the test administrator regarding movement of the handheld device during the gaze nystagmus test to assist in proper performance of the gaze nystagmus test.

16. The mobile telephony device of claim 15, wherein:
the program instructions computer-executable to implement providing a visual target on a handheld computing device further comprise program instructions computer-executable to implement activating a light source.

17. The mobile telephony device of claim 15, wherein:
the program instructions computer-executable to implement generating at least one test administrator signal from the handheld computing device further comprise program instructions computer-executable to implement generating at least one test administrator signal from the handheld computing device in response to an actuation of a first input on the handheld computing device by a test administrator.

18. The mobile telephony device of claim 15, further comprising:
program instructions computer-executable to implement recording movements of the handheld computing device during the gaze nystagmus test using a motion sensor within the handheld computing device.

19. The mobile telephony device of claim 15, wherein the program instructions computer-executable to implement generating at least one test administrator signal from the handheld computing device comprise program instructions computer-executable to implement generating audible sound through a speaker of the handheld computing device.

20. The mobile telephony device of claim 15, further comprising:
program instructions computer-executable to implement recording a video of eye movements of a test subject using a camera of the handheld computing device during the gaze nystagmus test.

* * * * *